United States Patent
Guynn et al.

(10) Patent No.: US 9,095,373 B2
(45) Date of Patent: Aug. 4, 2015

(54) SCRUB BRUSH

(71) Applicant: Tech Swerve LLC, Salt Lake City, UT (US)

(72) Inventors: John M. Guynn, Salt Lake City, UT (US); Branden D. Rosenhan, Salt Lake City, UT (US)

(73) Assignee: TECH SWERVE LLC, Salt Lake City, UT (US)

( * ) Notice: Subject to any disclaimer, the term of this patent is extended or adjusted under 35 U.S.C. 154(b) by 42 days.

(21) Appl. No.: 13/855,393

(22) Filed: Apr. 2, 2013

(65) Prior Publication Data

US 2013/0276251 A1  Oct. 24, 2013

Related U.S. Application Data

(60) Provisional application No. 61/635,112, filed on Apr. 18, 2012, provisional application No. 61/721,961, filed on Nov. 2, 2012.

(51) Int. Cl.

| A61B 19/00 | (2006.01) |
|---|---|
| A45D 29/17 | (2006.01) |
| A46B 9/02 | (2006.01) |
| A46B 11/00 | (2006.01) |
| A46B 15/00 | (2006.01) |
| A46B 5/00 | (2006.01) |
| A47K 7/02 | (2006.01) |
| A47K 7/03 | (2006.01) |

(52) U.S. Cl.
CPC .............. *A61B 19/36* (2013.01); *A45D 29/17* (2013.01); *A46B 5/0004* (2013.01); *A46B 5/0008* (2013.01); *A46B 9/02* (2013.01); *A46B 9/025* (2013.01); *A46B 15/0055* (2013.01); *A46B 11/00* (2013.01); *A46B 2200/1013* (2013.01); *A47K 7/02* (2013.01); *A47K 7/03* (2013.01)

(58) Field of Classification Search
USPC .............. 15/104.94, 106, 114, 167.3, DIG. 5, 15/DIG. 6; 132/73, 73.5, 75.3; 401/6, 24; D4/116, 119, 120
See application file for complete search history.

(56) References Cited

U.S. PATENT DOCUMENTS

| 1,052,312 | A | * | 2/1913 | Carling | ............................ 15/111 |
| 2,146,075 | A | * | 2/1939 | Kirsch | ............................ 15/106 |
| 2,223,204 | A | | 11/1940 | Carmichael | |
| D150,913 | S | * | 9/1948 | Wagner | .......................... D4/119 |
| 3,066,336 | A | | 12/1962 | Stobbe | |
| 3,354,492 | A | * | 11/1967 | Baumgartner | ............... 15/167.1 |
| 3,467,978 | A | * | 9/1969 | Golden | ............................ 15/111 |
| 3,744,078 | A | * | 7/1973 | Vallis | ............................ 15/167.3 |
| 3,843,991 | A | * | 10/1974 | Vallis | ............................ 15/167.3 |

(Continued)

*Primary Examiner* — Mark Spisich
(74) *Attorney, Agent, or Firm* — Workman Nydegger

(57) ABSTRACT

A scrub brush for cleaning arms, hands, and fingernails includes a reservoir for applying an antiseptic or cleaning composition and first and second groups of bristles having different relative flexibilities. The reservoir can be an absorbent open-foam material capable of absorbing and holding a liquid cleaning composition. The first bristles are designed to gently cleanse skin surfaces without scratching, gouging, scraping or otherwise damaging skin. The second bristles are more rigid than the first bristles to more aggressively scrub dirt, microbes or other foreign debris from gaps underneath fingernails. A finger alignment guide adjacent to the stiffer bristles maintains proper alignment between fingernails and the stiffer bristles so that the bristles enter gaps underneath the fingernails when the fingers are moved in a back and forth motion.

20 Claims, 7 Drawing Sheets

(56) References Cited

U.S. PATENT DOCUMENTS

| | | | | |
|---|---|---|---|---|
| D236,564 S | * | 9/1975 | Kaufman | D4/120 |
| 3,966,335 A | | 6/1976 | Abramson | |
| 4,130,908 A | | 12/1978 | Alcamo | |
| 4,137,929 A | | 2/1979 | Grossman | |
| 4,296,766 A | | 10/1981 | Benis | |
| 4,397,324 A | | 8/1983 | Thomas, Jr. | |
| 4,420,853 A | * | 12/1983 | Gilman et al. | 15/111 |
| 4,510,954 A | | 4/1985 | Miller | |
| 4,564,968 A | | 1/1986 | Buckley | |
| 4,646,953 A | | 3/1987 | Marshall et al. | |
| 4,730,949 A | * | 3/1988 | Wilson | 401/132 |
| 4,757,571 A | * | 7/1988 | Young | 15/167.3 |
| 4,915,331 A | | 4/1990 | Becker et al. | |
| 5,027,839 A | | 7/1991 | Appell | |
| 5,312,197 A | * | 5/1994 | Abramson | 401/6 |
| 5,442,829 A | * | 8/1995 | Summers | 15/106 |
| 5,500,971 A | | 3/1996 | Springmann | |
| 5,769,099 A | | 6/1998 | Davis et al. | |
| 5,855,212 A | | 1/1999 | Walker | |
| 6,016,812 A | | 1/2000 | Guynn | |
| 6,289,547 B1 | * | 9/2001 | Narula et al. | 15/167.3 |
| 6,324,716 B1 | * | 12/2001 | Holmes et al. | 15/113 |
| 7,260,863 B2 | * | 8/2007 | Kaufman et al. | 15/114 |
| 8,230,544 B2 | * | 7/2012 | Leshko | 15/160 |
| 2002/0002984 A1 | * | 1/2002 | Loy | 134/6 |
| 2003/0156884 A1 | * | 8/2003 | Teh | 401/39 |

* cited by examiner

SCRUB BRUSH

CROSS REFERENCE TO RELATED APPLICATION

This application claims the benefit of U.S. Provisional Application No. 61/635,112, filed Apr. 18, 2012, and entitled "MEDICAL SCRUB BRUSH," and also U.S. Provisional Application No. 61/721,961, filed Nov. 2, 2012, and entitled "MEDICAL SCRUB BRUSH," the disclosures of which are incorporated herein in their entirety.

BACKGROUND OF THE INVENTION

1. Field of the Invention

The invention is in the field of scrub brushes, more particularly surgical scrub brushes designed for cleaning and disinfecting a medical practitioner's hands and fingers, including the gap underneath the practitioner's fingernails.

2. Relevant Technology

Scrub brushes are commonly used to clean a person's arms and hands. In a surgical or other medial setting, doctors and other medical practitioners are required to scrub for a prescribed period of time to ensure complete sterilization of the arms and hands to prevent contamination of patients by e.g., bacteria, viruses and fungi.

A water moistened scrub brush is typically held with one hand and moved in a back and forth motion relative to the arms, hands and fingers of the other hand being cleaned. Cleansing detergents are used to help remove dirt and debris that are difficult to remove with water and mechanical scrubbing along. Sterilizing detergents and other agents can be used to kill pathogens in addition to being physically removed from the finger tips.

Detergents and soaps tend to be very slippery and can complicate the scrubbing process. Extreme care must be taken to maintain proper alignment between the slippery brush bristles and slippery finger tips while maintaining a vigorous back and forth scrubbing motion. Moreover, the bristles used in surgical scrub brushes are typically soft and flimsy by design in order to very lightly exfoliate an outer layer of skins from a medical practitioner's arms and hands. They are not designed for, and in fact are generally too soft and flimsy to clean the gap underneath a person's fingernails.

For this reason, state of the art surgical scrub brushes (e.g., BD E-Z scrub) are pre-packaged together with a separate tool for cleaning underneath the person's fingernails. The tool is molded from rigid plastic and is used much like a metal manicure blade or pocket knife to mechanically scrape dirt and debris from the gap under the fingernails. In practice, many surgeons and other medical practitioners do not use the fingernail cleaning tool because the process is time consuming and difficult, resulting on hands that are not fully sanitized or adequately sterilized prior to surgery or other medical procedures where sterilization is desired or critical.

BRIEF SUMMARY OF DISCLOSED EMBODIMENTS

Embodiments of the present invention are directed to improved hand held scrub brush devices that include a sponge preloaded with a cleaning composition (e.g., betadine or other agents known in the medical arts for cleaning and disinfecting hands), first flexible brush bristles designed to lightly exfoliate a person's arms and hands during a hand cleaning procedure, second more rigid brush bristles that are designed to scrub and remove dirt and other debris from underneath a person's fingernails, and a finger alignment guide that helps maintain a person's fingers in a defined spatial orientation relative to the second more rigid brush bristles in order to help maintain the person's finger tips in correct alignment with the second brush bristles while moving the hand and/or brush in a back and forth scrubbing motion relative to the person's finger tips.

According to one embodiment, a scrub brush includes a single finger alignment guide that includes a generally smooth guide surface that is substantially parallel to at least some of the bristles comprising the second more rigid brush bristles. This permits the user to lightly bear down on the smooth guide surface while moving the fingers and/or brush in a side to side motion. The presence of soap or liquid disinfectant can increase the lubricity of the guide surface in order to further reduce friction.

In another embodiment, the scrub brush can include a pair of finger alignment guides that cooperate to define a finger oscillation channel within which the fingers are maintained during the back and forth (or side to side) scrubbing motion. The finger alignment guides in this embodiment include a first wall or guide surface that engages the bottom surfaces of the fingers and a second wall or guide surface that engages the top surfaces of the fingers so as to define a finger oscillation channel that limits up and down motion. Limiting up and down motion further helps to maintain proper alignment of the fingers and the more rigid cleaning bristles and further reduces the amount of mental concentration and/or physical acumen required to maintain the fingers in proper alignment during the back and forth (or side to side) scrubbing action.

The finger guide structure may also include one or two end walls interconnecting the first and second walls or guide surfaces in order to further define a finger oscillation channel that limits side to side motion. Limiting side to side motion helps prevent the person's finger tips from slipping out of the oscillation channel defined by the first and second guide walls during vigorous scrubbing motion. In the case where the guide structure includes first, second and end walls, the guide structure provides a sleeve that essentially encloses the more rigid brush bristles on all sides. According to one embodiment, the sleeve extends beyond the ends of the brush bristle tips in order to define surfaces that maintain proper alignment of the person's finger tips and prevents them from slipping off during vigorous scrubbing action.

The top and bottom walls can be oriented so as to define a finger oscillating channel having a desired cross sectional shape. According to one embodiment, the first and second walls or guide surfaces can be substantially parallel to each other. In the case where the first and second walls are equally spaced above and below the mass of bristles, the scrub device can be held in either orientation (i.e., where the "top" wall is on the top or bottom during use).

According to another embodiment, the first and second walls can be angled relative to each other (i.e., in a divergent angle) in order to permit changing finger tip angulation during the scrubbing process. For example, in a first scrubbing motion, the bottom surface of fingers can bear against and slide across the first wall to provide a first angle of attack relative to the brush bristles. Thereafter, in a second scrubbing motion, the top surfaces of the fingers can be realigned to bear against and slide across the second wall to provide a second angle of attack relative to the brush bristles. Thus, the second wall provides an upper guide surface that permits a different contact angle between the bristles and finger tips when the top surfaces of the finger tips are urged against the top wall during the back and forth scrubbing motion.

The angle of the bristles relative to the top and bottom walls can be selected to provide a desired contact angle between the bristles and fingertips during the back and forth scrubbing motion. According to one embodiment, the scrubbing bristles are oriented so as to be substantially parallel to one or both of the first bottom and/or second wall surfaces. In another embodiment, the cleaning bristles have multiple angles to better clean under the fingernails regardless of finger angle.

In the event it is desired to clean other parts of a person's fingers, hands and arms, the finger alignment guide can be retractable in order to more fully expose the bristles for cleaning larger surfaces and body parts. In one embodiment, the alignment guide can be spring loaded in order to automatically retract upon depressing a button or engaging a latch device.

In one example, more rigid fingernail cleaning bristles and associated finger alignment guide comprised of one wall or a pair of spaced-apart walls (e.g., at a divergent angle) and can be provided around a perimeter of the scrub brush so as to be useable to clean under nails regardless of the orientation of the brush when gripped by a user's hand. The finger alignment guide can be positioned between the sponge and the more flexible brush bristles used to clean hands and arms. The more rigid fingernail cleaning bristles can extend approximately perpendicular relative to the more flexible bristles.

The scrub brush device can be rectangular in cross section, similar to existing surgical scrub-in devices. Alternatively, the scrub brush can have a curved (e.g., oval) cross-sectional shape.

The sponge element may be impregnated with a degreasing or other appropriate cleaning composition to aid in removing foreign debris from a person's hands and fingers in a more industrialized setting. The sponge element can have a substantially flat outer surface or it can be convex or concave as desired to provide a curved surface.

These and other advantages and features of the invention will become more fully apparent from the following description and appended claims, or may be learned by the practice of the invention as set forth hereinafter.

DETAILED DESCRIPTION OF THE PREFERRED EMBODIMENTS

I. Introduction

Disclosed herein are improved scrub brushes that incorporate different types of brush bristles, including softer arm and hand cleaning bristles for more gentle cleansing of a person's skin and stiffer fingernail cleaning bristles for more aggressive cleaning of dirt, bacteria, or other foreign debris from the gaps underneath a person's fingernails.

The brush bristles may comprise any appropriate polymer, metal or natural fiber material so long as they have a stiffness and/or flexibility suitable for either gently cleansing the skin of a person's arms and hands or more aggressively cleaning the gap underneath a person's fingernails (i.e. between the underside of the end portion of the fingernails and the adjacent detached skin portion of the fingers). The first and second brush bristles may comprise the same material or different materials, with lesser or greater stiffness being provided by at least one of the material properties of the bristle material, length, diameter, surface treatment, or chemical treatment of the bristle material. An example of a surface treatment to stiffen a more flexible bristle is applying a more rigid material over the surface of a softer underlying bristle material.

According to one embodiment, the first bristles for cleansing the skin of a person's arms and hands are sufficiently soft so as to promote gentle scrubbing action when the bristles are moved in a back and forth motion relative to the skin surfaces. The first bristles may be soft and flexible yet have enough sufficient stiffness or rigidity to promote or permit gentle surface exfoliation of the skin surfaces but without scratching, gouging, scraping or otherwise damaging the skin. This may be important in case of medical procedures when damage to the skin may cause greater risk of contamination or infection to the healthcare practitioner (e.g., by reducing the natural protection afforded by healthy skin). It may also be important to prevent blood, pieces of skin, or other foreign debris from being transferred from the healthcare practitioner to a patient or surgical site.

Figure 1:
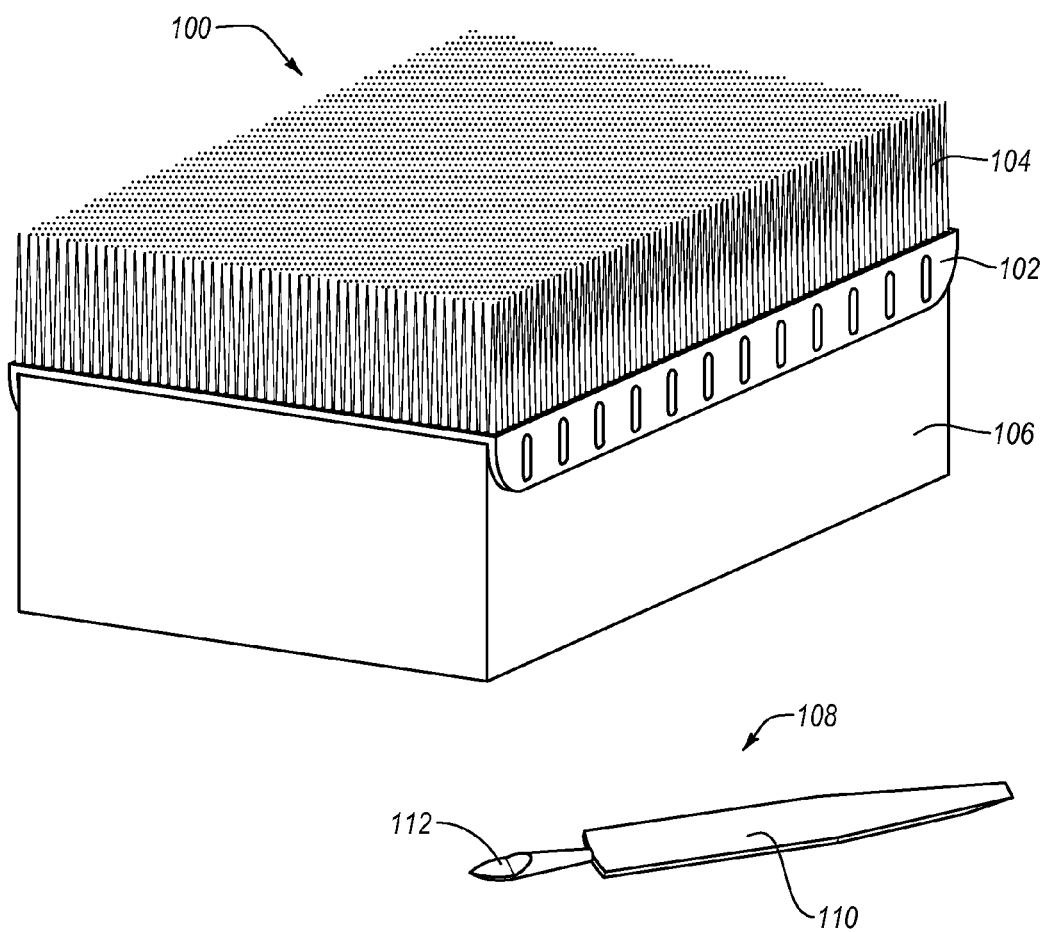
FIG. 1 is a perspective view of a common surgical scrub brush having a hand and arm washing member and a separate finger nail cleaning pick.

In general, the first bristles for cleansing the skin of a person's arms and hands are too soft and flexible to adequately clean dirt, bacteria, pathogens, or other foreign debris from the gap underneath a person's fingernails. In many cases, such as in state-of the art surgical scrub-in devices (e.g., as illustrated in FIG. 1), the arm and hand cleaning bristles are so soft and flexible as to be essentially incapable of entering the gap underneath the fingernails, at least not with sufficiently aggressive mechanical action to dislodge dirt, bacteria or other foreign debris. For this reason, a separate fingernail cleaning pick made of a rigid material is typically provided to permit the medical practitioner to separately clean underneath the fingernails apart from scrubbing arms and hands.

Examples of bristle materials for manufacturing cleaning bristles for use in the disclosed medical cleaning brushes include polyethylene, nylon, polyester, polypropylene, polystyrene, PEEK, polyvinyl chloride, acrylic, tetrafluoroethylene, silicone, animal fibers (e.g., goat hair, hog bristle, horse hair, ox hair, red sable, skunk, fitch, squirrel), vegetable fibers (e.g., bass, piassaya, palm, calabar, sherebro, bassine, kittool, palmetto, palmyra, rice root, zacatan, sisal, agave, union fiber (two or more materials), synthetic fibers (e.g., carbon fibers, glass, silica, ceramic, polyacrylonitrile, O-Pan, aramid, polymer impregnated with inorganic particles, such as silicon carbide particles, polymer with outer layer of inorganic material, such as copper sulfide), metal wire (e.g., aluminum, brass, phosphor bronze, stainless steel, nickel-titanium alloys, superelastic titanium alloys, nickel silver).

Examples of useful anti-infective compositions include at least one antiseptic selected from the group of betaine, chlorhexidine glutamate, iodine, povidone iodine, parachlorometaxylenol, chloroxylenol, triclosan, alcohols, quaternary ammonium compounds, cationic surfactants, anionic surfactants, phenol, polyhexanide, sodium chloride, boric acid, hydrogen peroxide, sodium hypochlorite, terpenes, and mixtures thereof.

II. Example Cleaning Scrub Brushes

Reference is now made to the drawings, which initially depicts a state of the art surgical scrub-in kit comprising a scrub-in brush and fingernail pick and thereafter shows embodiments of improved cleaning scrub brushes that permit faster, easier and more complete and total cleaning of a person's (e.g., medical practitioner's) arms, hands, and fingernails, including gaps underneath the fingernails.

FIG. 1 illustrates a common medical scrub-in kit comprising a surgical scrub-in brush 100 for washing a medical practitioner's hands and arms and a separate finger nail cleaning pick 108 for cleaning under the fingernails. The scrub-in brush 100 includes a rigid gripping structure 102 having side walls with molded ribs to enhance gripping by a medical practitioner during use. Individual rows and columns of integrally molded bristles 104 extend perpendicular from a top surface of rigid gripping structure 102. A flexible and liquid-absorbing sponge 106 is attached to a bottom surface of rigid gripping structure 102. Scrub-in brush 100 and nail pick 108 are typically pre-packaged within a sealed container (not shown) with a peel away cover. The side bristles are permanently deformed and bent toward the center of brush device as a result of bending forces by the sealed package.

Integrally molded bristles 104 are typically molded from a flexible polymer, such as polyethylene, to yield bristles that are highly flexible and limp in order to only lightly scrub the arms and hands during surgical scrub-in. A liquid antiseptic is initially stored within sponge 106. During scrub-in, the medical practitioner wets the arms and hands with water, applies the antiseptic to the arms and hands, and gently cleanses the arms and hands using sponge 106 and flexible bristles 104.

Flexible bristles 104 are too limp and flexible to clean underneath the fingernails. They lack rigidity and spring-back capability to perform this function. This lack of spring-back or resilience is evidenced by the fact that molded bristles 104 are bent inwardly by the sealed package but do not return to a perpendicular orientation when the surrounding package and bending forces are removed. Moreover, adjacent rows of bristles 104 are so flexible and limp as to provide no guiding function that would maintain a person's fingers and fingernails in a straight line relative to one or more rows or columns of bristles.

Because of the complete inability of flexible bristles 104 to effectively clean the gap underneath a medical practitioner's fingernails during a scrub-in procedure, it is necessary to perform a separate nail cleaning procedure using rigid nail cleaning pick 108, which includes a flat handle 110 that can be gripped by the user's hand in order to manipulate a curved nail cleaning point 112 and clean the gap underneath the nails of the other hand. This nail cleaning procedure is similar to using a rigid manicure tool or pocket knife to scrape dirt and debris from the gap under the fingernails. The instructions contained with typical scrub-in kits typically recommend first cleaning the fingernails before scrubbing the arms and hands. This is likely because cleaning the nails after sterilizing the arms and hand may contaminate the medical practitioner's hands with bacteria, dirt, and other foreign debris removed from the gap under the nails.

Anecdotal evidence indicates that the standard cleaning procedure using nail cleaning pick 108 is inadequate to clean and sterilize under the fingernails, which can be a source of contamination of a patient or surgical site. First, notwithstanding clear instructions on the scrub-in package to first clean underneath the fingernails, evidence suggests that many (if not most) surgeons and practitioners ignore this instruction and simply discard the nail cleaning pick and only use the scrub-in brush to sterilize the arms and hands. Assuming that it takes only six seconds to clean under each fingernail, cleaning under all ten (10) nails would take a full minute to complete. Many practitioners consider this a waste of precious time and not worth the effort and hassle required to properly complete the recommended nail cleaning procedure. Second, even if the practitioner actually follows the recommended procedure, it may still be inadequate to effectively disinfect the gap under the nails. There is typically no recommendation to first apply antiseptic to the finger tips and under the nails before using the nail cleaning pick. As a result, the nails are cleaned in a "raw" unsterilized condition. Moreover, dirt, bacteria and other debris can cross-contaminate from dirtier nails cleaned initially to subsequent nails that may initially have been cleaner to start with, which may make the procedure worse than doing nothing (which is what many practitioners do anyway).

Regardless of the reason for not effectively using the nail cleaning pick, the inventors have identified serious problems and flaws with existing scrub-in kits and procedures, which have heretofore not been recognized or addressed, and propose a solution to this previously unrecognized problem in order to facilitate cleaning and sterilizing the gaps underneath a medical practitioner's fingernails. The disclosed cleaning scrub brushes and methods greatly reduce time and effort required to clean underneath the fingernails and promote increased user compliance, which will result in cleaner, more sterile fingernails compared to state of the art scrub-in devices and methods.

Figure 2A:
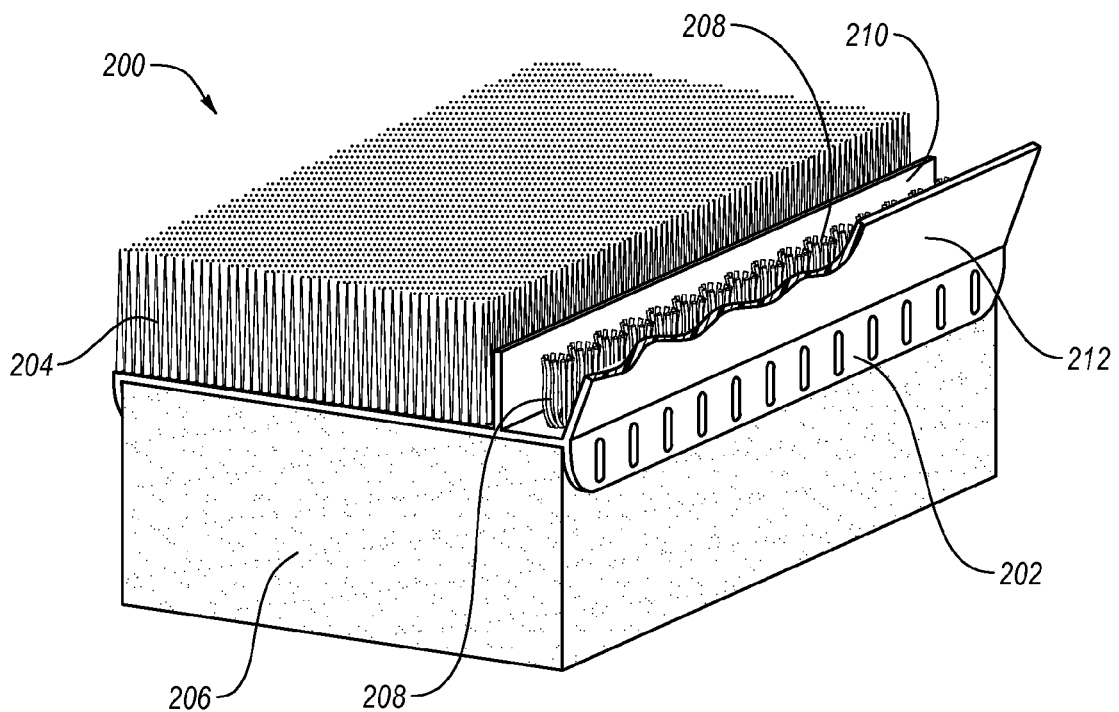
FIG. 2A is a perspective view of an improved scrub brush according to one embodiment, which includes first arm and hand washing bristles, a cleaning or disinfecting sponge, fingernail cleaning bristles in a first orientation, and a guide surface.

FIG. 2A illustrates a first embodiment of an improved scrub brush 200, which includes a structural body 202, which can interconnect other components of scrub brush 200, and which can be gripped by the medical practitioner during use. According to one embodiment, structural body 202 forms a relatively rigid skeletal frame to which softer, more flexible components can be attached. For example, structural body 202 can be molded from a polymer material to form the relatively rigid skeletal frame. Ribs, recesses or other grip-enhancing features can be molded into, embedded in, or attached the sides of the structural body to further enhance gripping by the user.

Structural body 202 may further include a continuous or discontinuous scaffold-like structure spanning substantially across a length and width of scrub brush 200. As further illustrated in FIG. 2A, a first side of structural body 202 may provide a first surface or platform from which flexible arm and hand scrubbing bristles 204 extend. Bristles 204 may form uniform rows and columns and extend substantially perpendicularly from the first side of structural body 202, at least at the interface between structural body 202 and bristles 204. According to one embodiment, arm and hand scrubbing bristles 204 are cone-shaped structures co-molded with structural body 202 to form a single continuous piece of material (e.g., polymer). Arm and hand cleaning bristles 204 are advantageously made from a relatively soft polymer, such as polyethylene, in order to only provide light scrubbing action to a user's skin, perhaps only enough to lightly cleanse and exfoliate loose outer skin but without scratching, gouging, scraping or otherwise damaging the skin. Structural body 202 can be made from the same or different material. Stiffness of structural body 202 can be increased relative to bristles 204 by increasing thickness of structural body 202, molding from a different material, adding or attaching stiffer material, or treating the polymer.

In some cases, bristles 204 may continue straight and remain substantially perpendicular from the interface to cleaning tips at the opposite ends of bristles 204. FIG. 2A shows this idealized version of the device. In practice, arm and hand cleaning 204 bristles may become bent and permanently deformed when placed in a sealed package prior to use, similar to existing surgical scrub-in brushes. Bristles 204 may all have the same length, or different regions of bristles 204 may have different lengths (e.g., longer around a perimeter and shorter in the center).

As further illustrated in FIG. 2A, a second side of the structural body 202 may provide a second surface or platform to which an antiseptic reservoir 206 is attached. Reservoir 206 can be adhered to structural body 202 by adhesive and/or by mechanical means, such as protrusions that fit within corresponding recesses or depressions. Sides of structural body can wrap around and partially enclose a portion of reservoir 206 to assist in preventing dislodgment of the reservoir during use. Antiseptic reservoir 206 advantageously comprises an absorbent material capable of absorbing and holding therein a liquid disinfectant composition or solution. According to one embodiment, antiseptic reservoir 206 comprises a soft, flexible, liquid-absorbent, open cell foam material. Examples of absorbent sponge or sponge-like materials that can used to form antiseptic reservoir 206 include synthetic sponges, low-density polyether, polyvinyl alcohol (PVA) (a very dense, highly absorbent material with no visible pores) and polyester. Polyester sponges may be sub-divided into a variety of types, some being reticulated (artificially broken-in) for ease of use. Other types are double-blown polyester, meaning that they have high water retention ability, approaching or equaling PVA, but with visible pores and more flexibility of applications. Antiseptic reservoir 206 can have a flat or curved outer surface (e.g., convex or concave).

Prior to use, antiseptic reservoir 206 holds therein a measured quantity of an anti-infective composition, such as a liquid antiseptic that is absorbed into a sponge or sponge-like structure of antiseptic reservoir 206. In use, the liquid antiseptic can be dispensed onto the user's arms and hands, such as by squeezing the flexible structure of antiseptic reservoir 206 and/or wetting it with water and permitting or causing diluted antiseptic solution to wet the skin of the user's arms and hands. The antiseptic from antiseptic reservoir 206 can be used to both clean and disinfect a medical practitioner's hands as well as assist in cleaning and disinfecting the gap underneath the medical practitioner's fingernails.

As further illustrated in FIG. 2A, brush device 200 further includes specialized fingernail cleaning bristles 208 different from arm and hand cleaning bristles 204. According to one embodiment, fingernail cleaning bristles 208 are characterized as being substantially stiffer and more mechanically rigid than arm and hand cleaning bristles 204. This permits or causes fingernail cleaning bristles 208 to more aggressively scrub dirt, microbes, pathogens, or other foreign debris from the gaps underneath the user's fingernails during use (as compared to softer arm and hand bristles 204), such as when the person's fingers are moved back and forth relative to the fingernail cleaning bristles. It will be appreciated that such back and forth motion of the person's fingers is equivalent to moving both the fingers and brush device 200 in concert (i.e., in opposite directions in each back and forth cycle). It is also equivalent to keeping the fingers stationary and only moving brush device 200. In reality, one or both may be moved depending on the particular scrubbing habits of the user.

According to one embodiment, bristles 208 are made from a stiffer material than bristles 204. For example, bristles 204, 208 can both be co-molded together with the structural body 202 but using different polymers to make softer arm and hand cleaning bristles 204, on the one hand, and stiffer fingernail cleaning bristles 208, on the other. Alternatively, bristles 204, 208 can be made from the same polymer material, but formed with different lengths and/or thicknesses to alter stiffness. For example, bristles 208 can be shorter and thicker, while bristles 204 can be longer and thinner. Alternatively or in addition, bristles 208 can be treated, coated and/or infused with a material that makes them stiffer than bristles 204 and/or bristles 204 can be treated and/or infused with a softening material that makes them softer than bristles 208. Fingernail cleaning bristles 208 can be formed separately from structural body 202 and later attached, such as by adhering a bristle support member (not shown) to structural body 202, to which bristles 208 are formed or with which they are co-molded. Bristles 208 can be inserted into recesses formed in structural body 202, either individually or in bundles.

According to one embodiment, fingernail cleaning bristles 208 are aligned in one or more rows adjacent to one or more finger alignment guides having alignment surfaces. As illustrated in FIG. 2A, scrub brush 200 may include a first finger alignment guide 210 having a smooth, low friction surface, and a second alignment guide 212 having a smooth, low friction surface, which are spaced-apart and cooperate to form a finger guide channel within which fingernail cleaning bristles 208 are disposed. The one or more alignment guides can be co-molded with structural body 202 using the same or different materials (e.g., thermoplastic, such as polypropylene, polystyrene, PVA, acrylic). Alternatively, the one or more alignment guides can be formed separately, such as co-molding or assembled together with finger cleaning bristles 208, and then attached to structural body 202 (e.g., using adhesive or thermoplastic welding).

Figure 2B:
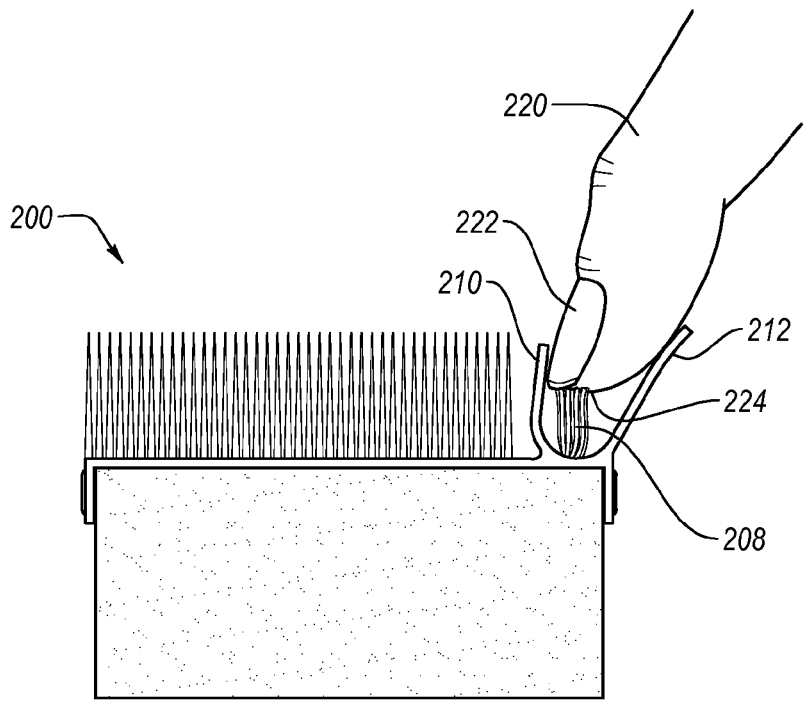
FIG. 2B is a side view of the scrub brush of FIG. 1A with a finger engaging the guide surface and fingernail cleaning bristles.

As illustrated in FIG. 2B, a bottom surface 222 of a finger 220 can contact and rub against second alignment surface 212 in order to maintain finger 220 in a proper orientation relative to fingernail cleaning bristles 208 in order for ends and/or tips of bristles 208 to enter gap 224 underneath fingernail 222. According to one embodiment, second alignment structure 212 can be more rigid than first alignment structure 210. Alternatively, first alignment structure 210 can be omitted entirely or made more flexible in order to reduce or eliminate the possibility of scraping a user's skin while scrubbing arms or hands. In yet another embodiment, second alignment structure 212 can be omitted and only first alignment structure 210 is used to align fingers with fingernail cleaning bristles 208.

Fingernail cleaning bristles 208 can be of uniform or varying length to affect their ability to enter the gaps under a person's fingernails. They can be parallel, angled, convergent, divergent, and combinations thereof to provide varying cleaning actions. For example, bristles 208 may include regions of varying length in order to accommodate fingers of different length and/or the curvature of fingernail gaps. In one embodiment, a region of fingernail cleaning bristles 208 at one or both ends of cleaning scrub brush 200 can be longer to better reach and clean fingernails of short fingers (e.g., index finger and/or pinky). A middle region of bristles 208 can be shorter to account for longer middle and ring fingers, with the shortest bristles being used to clean under the nail of the middle finger. Bristles 208 can also have varying length to form a curved or semi-circular tip interface to account for the natural curvature of the fingernail gaps, with shorter bristles for cleaning the middle of the gap and longer bristles for cleaning the sides. Bristles 208 and associated finger alignment guide(s) can be disposed on one or more sides of brush 200 and/or around a perimeter of brush 200.

Similar effects can be accomplished by including longer and shorter bristles interspersed together (e.g., random or alternating) and/or interspersing or alternating bristles of varying angle, stiffness. Moreover, gaps or divisions between adjacent plugs or groupings of bristles 208, as shown in FIG. 2A, can permit the edge bristles of each plug or bristle grouping to reach into the outer regions of a curved fingernail gap as the fingers are moved back and forth relative to the fingernail cleaning bristles 208. Bristles of varying, random or changing angle can be provided to increase the contact angle and/or aggressiveness of the bristles, such as to accommodate natural curvatures or other variations in the size, shape and/or position of the fingernail gap(s) relative to the ends or tips of bristles 208.

In use, a medical practitioner can clean fingernail gaps one at a time or, alternatively, multiple fingernail gaps simultaneously using the same back and forth scrubbing action. In some cases, all four fingers of each hand can be cleaned simultaneously, with the thumbs cleaned separately. This greatly facilitates and shortens the time required to clean under the fingernails compared to using a fingernail pick, which can only clean one nail at a time and generally requires more concentration, effort, and physical dexterity compared to cleaning nails using the disclosed devices. Because the user's nails can be cleaned in a fraction of the time (e.g., less than half, one-third, or one-fourth the time) and with less effort and hassle compared to using a fingernail pick, this should increase user compliance. The nails can be cleaned using the same device and with a similar scrubbing action as when cleaning the arms and hands, which permits total cleaning and disinfecting using a single device, rather than two, which further increases user compliance. Moreover, because fingernail gaps can be cleaned before and/or after cleaning the hands and arms using the same disinfecting composition and/or under running water, greater sterility can generally be obtained as compared to using a fingernail pick. While the fingernail pick uses only mechanical cleaning action, the dedicated fingernail cleaning bristles 208, coupled with use of the antiseptic composition from antiseptic reservoir 204, combines mechanical and chemical cleaning action, which can ensure greater cleaning and sterility. And it accomplishes both with less effort and in less time compared to a fingernail pick. This is a surprising and unexpected result compared to state of the art surgical scrub-in systems and procedures.

Figure 3A:
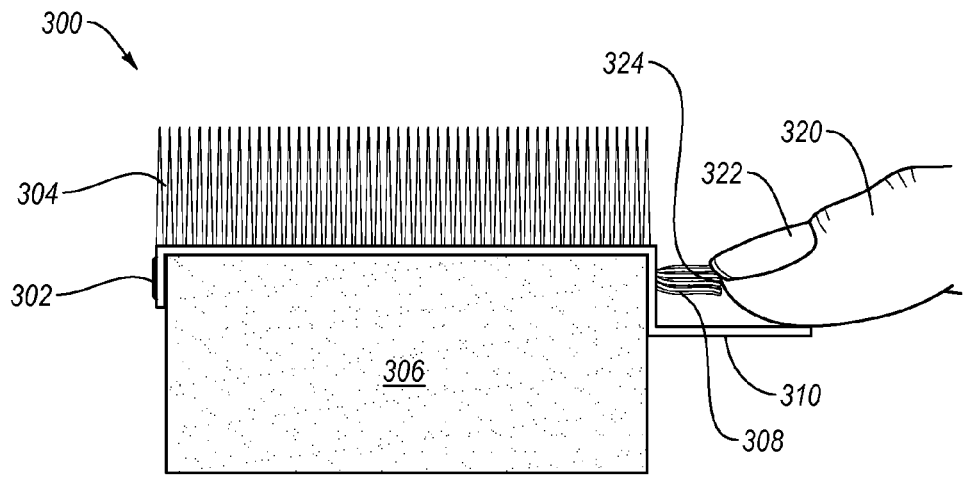
FIG. 3A is a side view of a second embodiment of an improved scrub brush in which the fingernail cleaning bristles and guide surface have second alternative orientations.
Figure 3B:
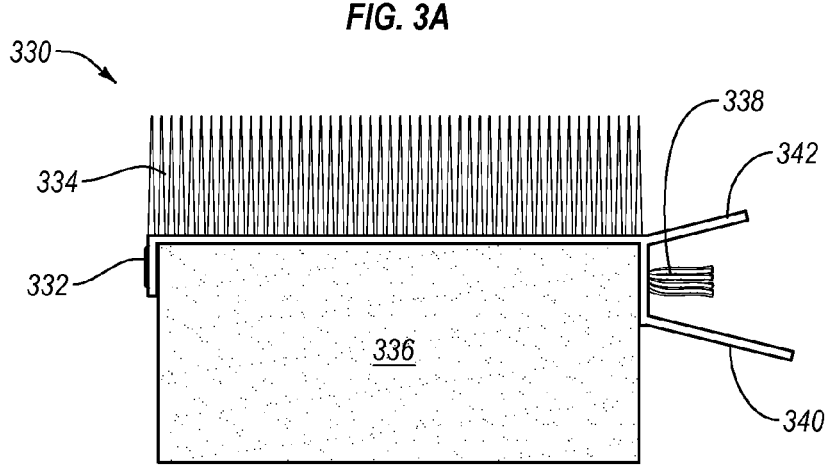
FIG. 3B is a side view of a variation of the embodiment shown in FIG. 3A but which includes a second guide surface that cooperates with the first guide surface to create a guide channel within which the fingernail cleaning bristles are positioned.
Figure 3C:
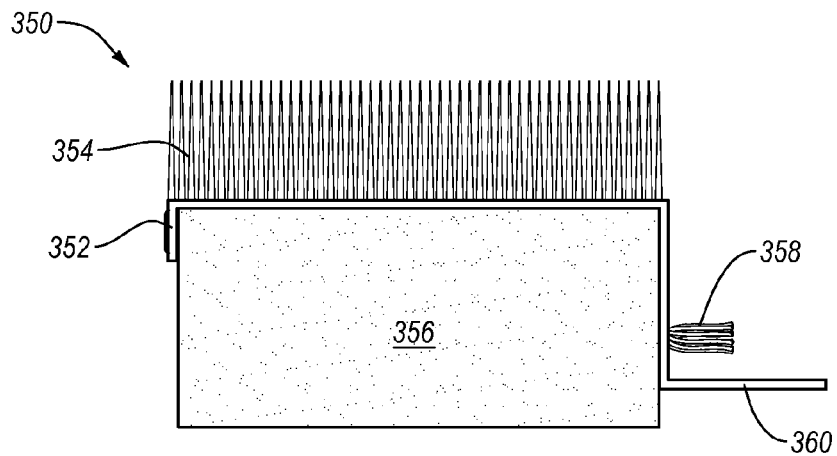
FIG. 3C is a side view of a variation of the embodiment shown in FIG. 3A in which the guide surface is positioned closer to a surface of the cleaning or disinfecting sponge.

FIGS. 3A-3C illustrate alternative embodiments of a scrub brush in which the fingernail cleaning bristles extend from a different side or region of the device than the arm and hand cleaning bristles.

In FIG. 3A, a scrub brush 300 includes a structural body or skeleton 302 with sides that can be engaged by a user during a cleaning procedure. Arm and hand cleaning bristles 304 extend from a first side or surface of structural body 302. An antiseptic reservoir 306 is positioned against a second opposite side or surface. As illustrated in FIG. 3A, fingernail cleaning bristles 308 can extend from a side surface of structural body 302. They can be co-molded with or attached to the structural body 302 depending on the manufacturing method. A finger alignment guide or surface 310 is provided adjacent to bristles 308 in order to help maintain a user's finger 320 and fingernail 322 in proper alignment to facilitate entry of the ends or tips of bristles 308 into gap 324 underneath the fingernail 322 and effect cleaning.

FIG. 3B illustrates an alternative embodiment of a scrub brush 330 having a structural body 332, arm and hand cleaning bristles 334, antiseptic reservoir 336, fingernail cleaning bristles 338, first finger alignment guide 340, and second finger alignment guide 342 which cooperates with first finger alignment guide 340 to form a finger alignment channel partially enclosing fingernail cleaning bristles 338. First finger alignment guide 340 can be the same length or longer than second finger alignment guide 342. Either may be used as desired to maintain proper alignment between fingers and bristles 338 to facilitate cleaning and disinfecting of the gaps under a user's fingernails. For example, a person may position and rub the bottom surfaces of the user's fingers against second alignment guide 342, while the first finger alignment guide 340 engages top surfaces of fingernails as needed to maintain proper alignment with the bristles 338.

FIG. 3C illustrates another alternative embodiment of a scrub brush 350 having a structural body 352, arm and hand cleaning bristles 354, antiseptic reservoir 356, fingernail cleaning bristles 358, and finger alignment guide 360, which is positioned so as to help maintain a user's fingers in proper alignment with fingernail bristles 358 to facilitate cleaning of gaps underneath the fingernails. One difference between the embodiments illustrated in FIGS. 3A and 3C is that finger alignment guide 360 is positioned further down from the surface of the structural body 352 from which the arm and hand cleaning bristles 354 extend. This may help a user to grip structural body 352, both while scrubbing the arms and hands and cleaning the fingernails (e.g., because there will be a larger exposed gripping surface on a side of structural body 352 opposite the other surface). In similar fashion, finger alignment guides 340, 342 and channel shown in FIG. 3B can be moved further down the side of structural body 332 to provide additional gripping surface.

Figure 4A:
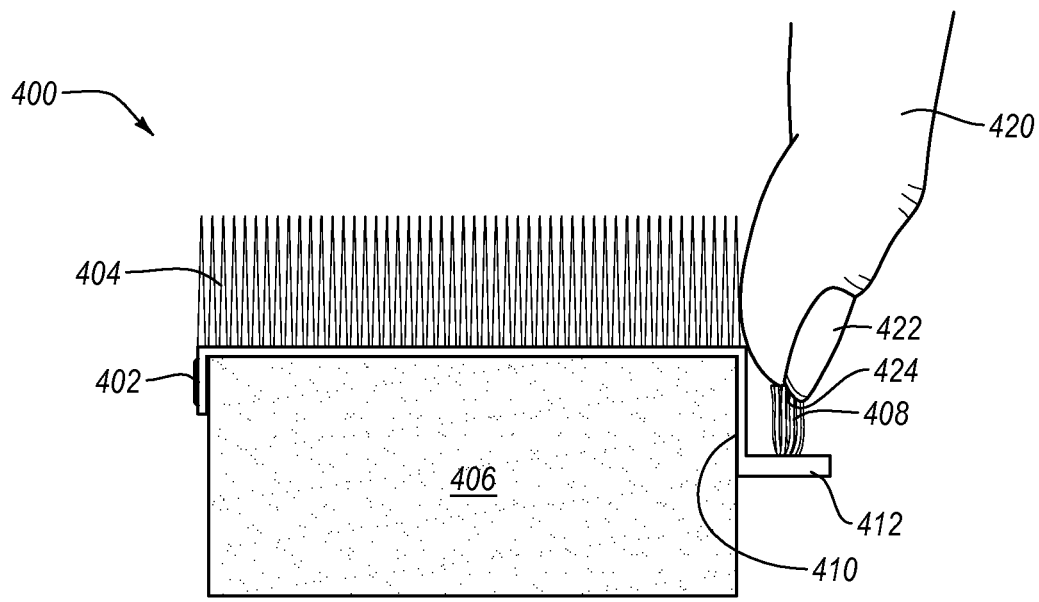
FIG. 4A is a side view of a third embodiment of an improved scrub brush in which the fingernail cleaning bristles and guide surface have third alternative orientations.
Figure 4B:
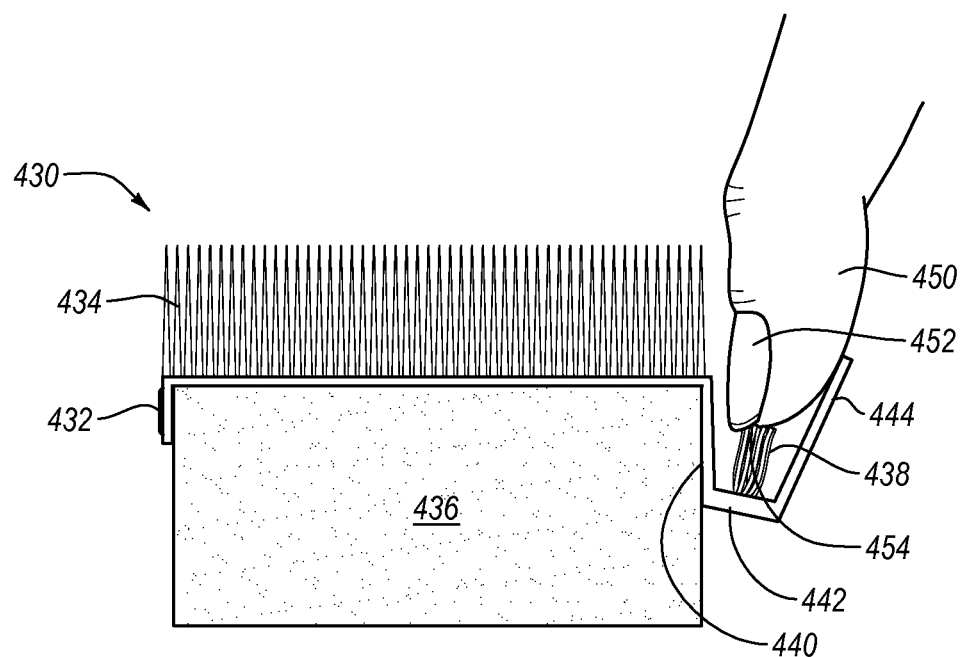
FIG. 4B is a side view of a variation of the embodiment shown in FIG. 4A but which includes a second guide surface that cooperates with the first guide surface to create a guide channel within which the fingernail cleaning bristles are positioned.

FIGS. 4A and 4B illustrate alternative embodiments of a scrub brush in which the fingernail cleaning bristles are elevationally offset relative to the arm and hand cleaning bristles but extend in the same general direction.

In FIG. 4A, a scrub brush 400 includes a structural body or skeleton 402 with sides that can be engaged by a user during a cleaning procedure. Arm and hand cleaning bristles 404 extend from a first side or surface of structural body 402. An antiseptic reservoir 406 is positioned against a second opposite side or surface. As illustrated in FIG. 4A, fingernail cleaning bristles 408 can extend from a bristle support platform 412 extending from a side surface 410 of structural body 402. The bristles 408 and/or support platform 412 can be co-molded or assembled with the structural body 402 depending on the manufacturing method. Side surface 410 of structural body 402 can function as a finger alignment guide and provide a smooth, generally low friction surface adjacent to bristles 408 in order to help maintain a user's finger 420 and fingernail 422 in proper alignment to facilitate entry of the ends or tips of bristles 408 into gap 424 underneath fingernail 422 and effect cleaning.

FIG. 4B illustrates an alternative embodiment of a scrub brush 430 having a structural body 432, arm and hand cleaning bristles 434, antiseptic reservoir 436, fingernail cleaning bristles 438, first finger alignment guide surface 440, bristle support platform 442, and second finger alignment guide 444, which cooperates with first finger alignment guide surface 440 to form a finger alignment channel partially enclosing fingernail cleaning bristles 438. Second finger alignment guide 444 can be the same length, shorter, or longer than first alignment surface 440 (e.g., second alignment guide 444 can be shorter than first alignment surface 440 if the bristle platform 442 is moved further down the side of brush 430). Either guide surface 440, 444 may be used as desired to maintain proper alignment between a user's finger(s) 450 and fingernail(s) 452 and bristles 438 to facilitate cleaning and disinfecting of gap(s) 454 under fingernail(s) 452. For example, a person may position and rub the bottom surfaces of the user's fingers against second alignment guide 444, while the first alignment surface 440 engages top surfaces of fingernails as needed to maintain proper alignment with the bristles 438. Alternatively, the position of the fingers can be reversed in order for bottom surfaces to engage and slide against first alignment surface 440 while second alignment guide 444 engages top surfaces of fingernails as needed to maintain proper alignment with bristles 438.

Figure 5A:
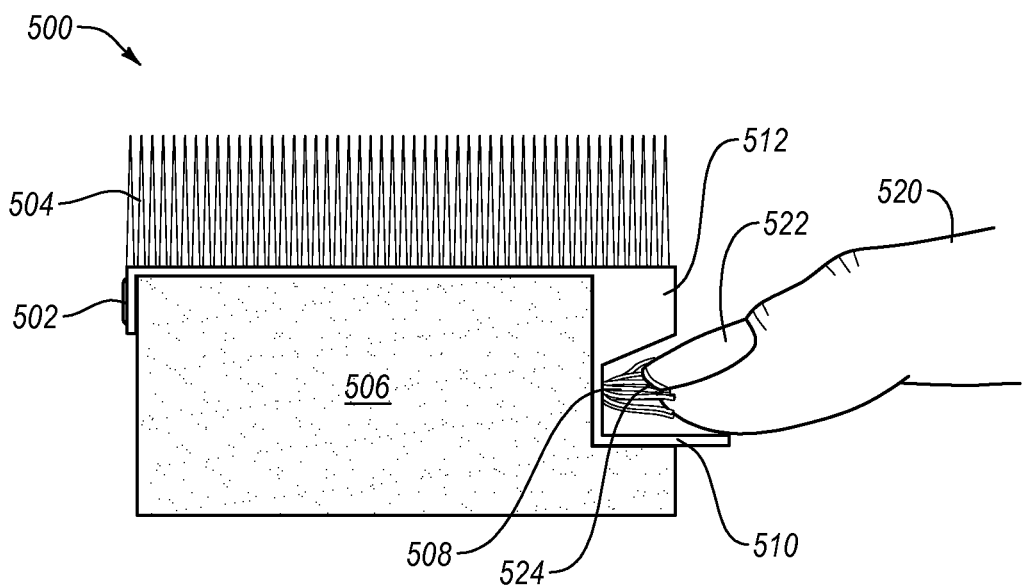
FIG. 5A is a side view of a fourth embodiment of an improved scrub brush in which the fingernail cleaning bristles and guide surface have fourth alternative orientations.
Figure 5B:
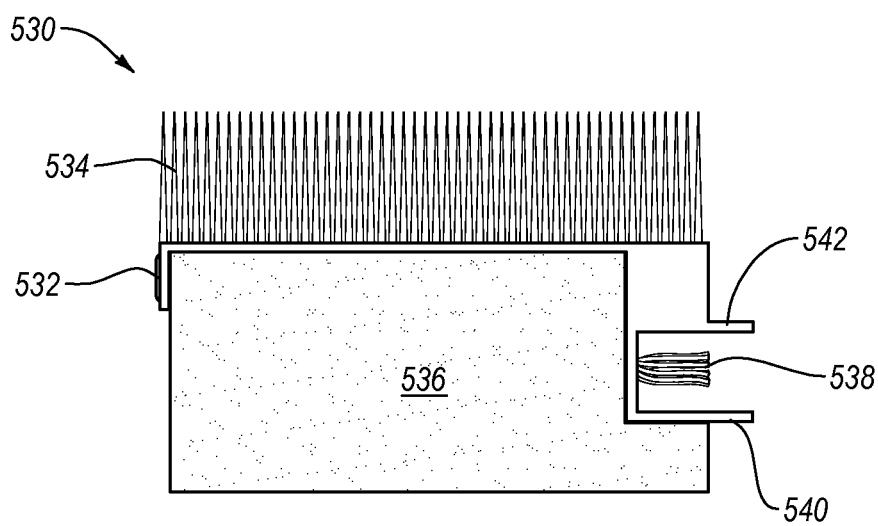
FIG. 5B is a side view of a variation of the embodiment shown in FIG. 5A but which includes a second guide surface extension that cooperates with the first guide surface to create a guide channel within which the fingernail cleaning bristles are positioned.

FIGS. 5A and 5B illustrate alternative embodiments of a scrub brush in which the fingernail cleaning bristles are recessed within a side of the device.

In FIG. 5A, a scrub brush 500 includes a structural body or skeleton 502 with sides that can be engaged by a user during a cleaning procedure. Arm and hand cleaning bristles 504 extend from a first side or surface of structural body 502. An antiseptic reservoir 506 is positioned against a second opposite side or surface of structural body 502. As illustrated in FIG. 5A, fingernail cleaning bristles 508 can be at least partially positioned within a recessed portion of structural body 502. A finger alignment guide or platform 510 extends laterally from a side of structural body 502 to partially enclose bristles 508 on one side and an opposing region 512 of structural element 502 having an angled surface partially enclose bristles 508 on another side for form a finger alignment channel partially enclosing fingernail cleaning bristles 508. In use, finger alignment guide or platform 510 can support the bottom surface of finger 520 to maintain proper alignment of fingernail 522 with fingernail cleaning bristles 508 to help maintain proper alignment between the fingernail 522 and bristles 508 to facilitate cleaning and disinfecting the gap 524 underneath the fingernail 532.

FIG. 5B illustrates an alternative embodiment of a scrub brush 530 having a structural body 532, arm and hand cleaning bristles 534, antiseptic reservoir 536, fingernail cleaning bristles 538 positioned within a recessed finger alignment channel within the structural body 532, first finger alignment guide surface 540, and second finger alignment guide surface 542, which cooperates with first finger alignment guide surface 540 to form the recessed finger alignment channel partially enclosing fingernail cleaning bristles 538. Finger alignment surfaces 540, 542 can be the same length, shorter, or longer as desired. They may extend beyond a surface of the structural body as shown, or they may terminate at the surface (not shown).

Either finger alignment surface 540, 542 may be used as desired to maintain proper alignment between a user's finger(s) and fingernail(s) and bristles 538 to facilitate cleaning and disinfecting of the gap(s) under the fingernail(s). For example, a person may position and rub the bottom surfaces of the user's fingers against first alignment surface 540, while second alignment surface 542 engages top surfaces of fingers or fingernails to maintain proper alignment with bristles 538. Alternatively, the position of the fingers can be reversed in order for bottom surfaces to engage and slide against second alignment surface 542 while first alignment surface 540 engages top surfaces of fingers or fingernails to maintain proper alignment with bristles 538.

Figure 6A:
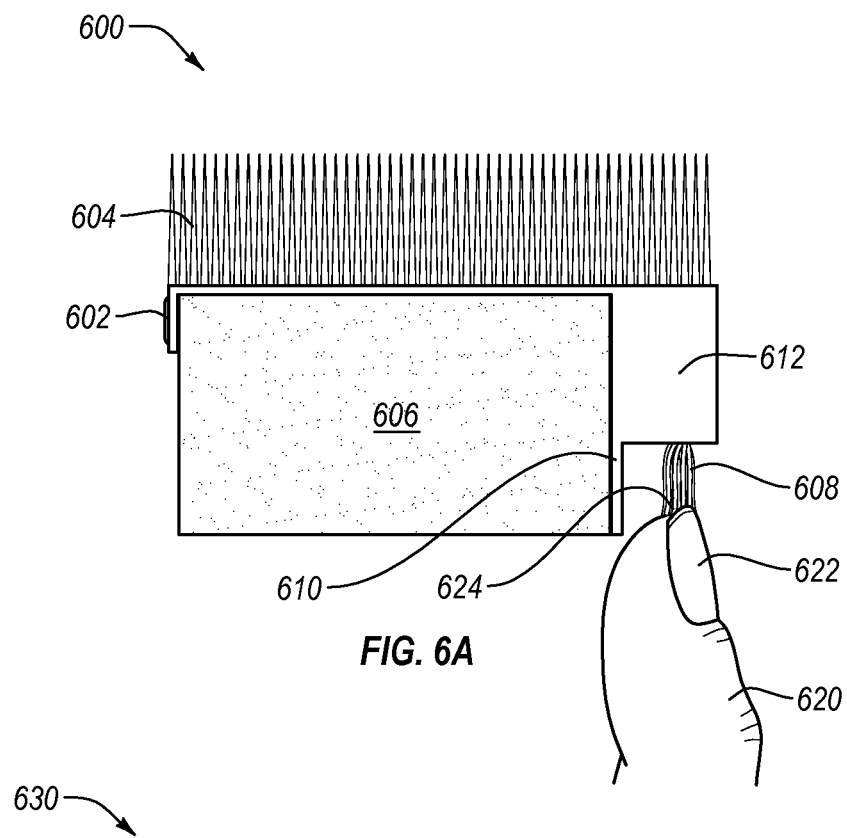
FIG. 6A is a side view of a fifth embodiment of an improved scrub brush in which the fingernail cleaning bristles and guide surface have fifth alternative orientations.
Figure 6B:
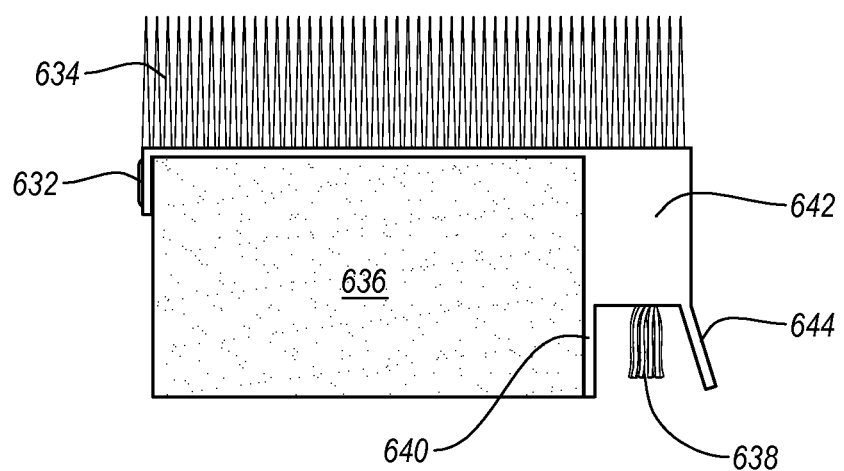
FIG. 6B is a side view of a variation of the embodiment shown in FIG. 6A but which includes a second guide surface extension that cooperates with the first guide surface to create a guide channel within which the fingernail cleaning bristles are positioned.

FIGS. 6A and 6B illustrate alternative embodiments of a scrub brush in which the fingernail cleaning bristles are elevationally offset relative to the arm and hand cleaning bristles and extend generally in an opposite direction.

In FIG. 6A, a scrub brush 600 includes a structural body 602 with sides that can be engaged by a user during a cleaning procedure. Arm and hand cleaning bristles 604 extend from a first side or surface of structural body 602. An antiseptic reservoir 606 is positioned against a second opposite side or surface of structural body 602. As illustrated in FIG. 6A, fingernail cleaning bristles 608 can extend from a bristle support platform 612 recessed into (or extending from) a side of structural body 602. As shown in FIG. 6A, support platform 612 can support both hand cleaning bristles 604 and fingernail cleaning bristles 608 positioned on opposite sides of platform 612. In this way, scrub brush 600 can maintain a more rectangular cross section throughout most of the device with minimal protrusions, recesses or discontinuities as compared to the embodiments shown in FIGS. 2-5. This may simplify manufacture, packaging and use of the device. In use, a finger alignment surface 610 on a side of structural body 602 can help maintain a user's finger(s) 620 and fingernail(s) 622 in proper alignment with finger cleaning bristles 608 and facilitate entry of the ends or tips of bristles 608 into gap(s) 624 underneath fingernail(s) 622.

FIG. 6B illustrates an alternative embodiment of a scrub brush 630 having a structural body 632, arm and hand cleaning bristles 634, antiseptic reservoir 636, fingernail cleaning bristles 638, and a bristle support platform 644 recessed into (or extending from) a side of structural body 632. A finger alignment channel defined by first finger alignment guide surface 640 and second finger alignment guide surface 644 partially encloses fingernail cleaning bristles 638. Second finger alignment guide surface 644 can be the same length, shorter, or longer than first alignment guide surface 640. For example, second alignment guide surface 644 can be shorter than first alignment guide surface 640 if bristle platform 642 and fingernail cleaning bristles 638 are moved closer to the arm and hand cleaning bristles 634. Alternatively, second alignment guide surface 644 can extend beyond a bottom surface of antiseptic reservoir 636 and thereby be longer than first alignment guide surface 640.

In use, either guide surface 640, 644 may be used as desired to maintain proper alignment between a user's finger(s) and fingernail(s) and bristles 638 to facilitate cleaning and disinfecting of the gap(s) under the fingernail(s). For example, a person may position and rub the bottom surfaces of the user's fingers against second alignment guide surface 644, while first alignment guide surface 640 engages top surfaces of fingernails to maintain proper alignment with bristles 638. Alternatively, the position of the fingers can be reversed in order for bottom surfaces to engage and slide against first alignment guide surface 640 while second alignment guide surface 644 engages top surfaces of fingernails to maintain proper alignment with bristles 638.

In an alternative embodiment (not shown), first alignment guide surface 640 can be partially or wholly eliminated by positioning finger cleaning bristles 638 at or near the bottom of disinfectant reservoir 636. The second alignment guide 644 would then extend beyond the bottom surface of disinfectant reservoir 636 and provide the main or sole finger guide surface.

Figure 7:
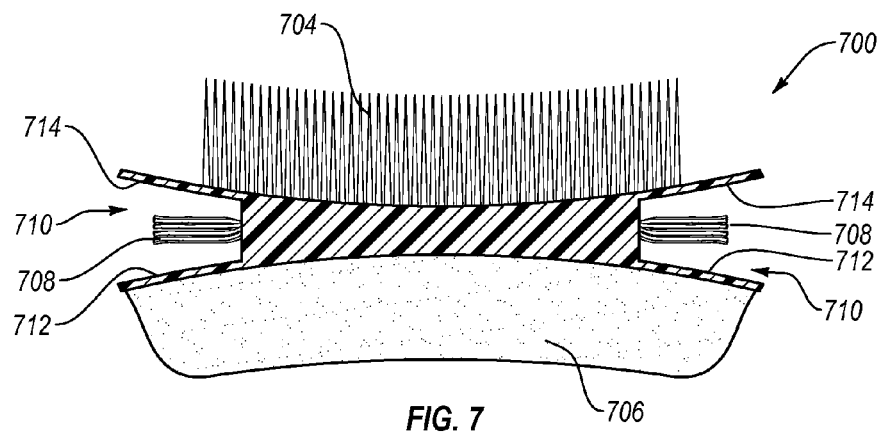
FIG. 7 is a cross-sectional view of an example scrub brush that includes fingernail cleaning bristles and opposing guide surfaces around a perimeter of the scrub brush.

FIGS. 7 and 8 illustrate example scrub brushes 700, 800 in which more rigid fingernail cleaning bristles 708, 808 and an associated finger alignment guide 710, 810 comprised of one wall or a pair of spaced-apart walls 712, 714 (e.g., at a divergent angle) can be provided around a perimeter of scrub brushes 700, 800 so as to be useable to clean under nails regardless of the orientation of scrub brushes 700, 800 when gripped by a user's hand during use. As further illustrated in FIG. 7, finger alignment guide 710 can be positioned between sponge 706 and more flexible brush bristles 704 used to clean hands and arms. The more rigid fingernail cleaning bristles 708 can extend approximately perpendicular relative to more flexible bristles 704.

Figure 8A:
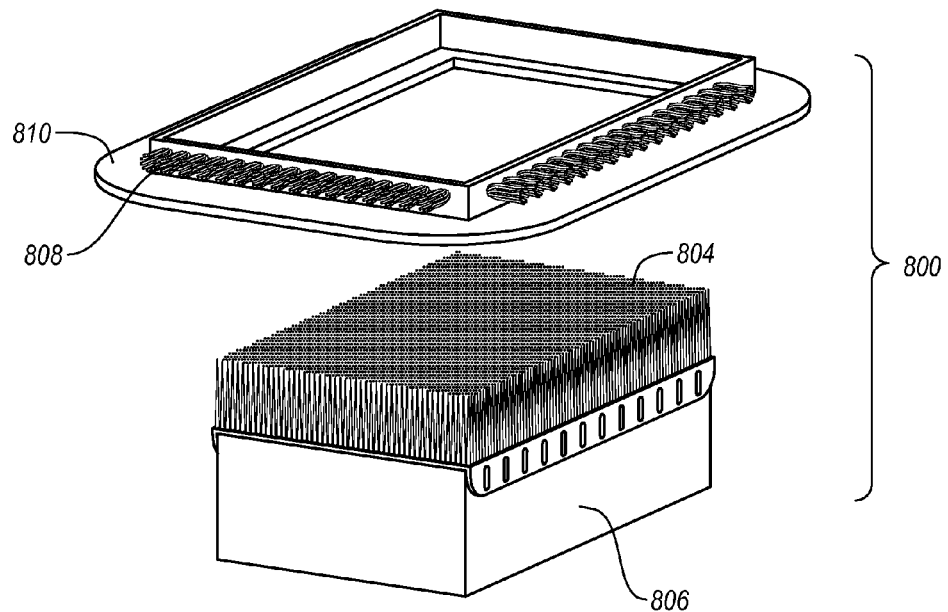
FIGS. 8A and 8B illustrate an example scrub brush having an oval cross-sectional shape and that includes a first part composed of the sponge and softer bristles and a second part composed of the finger alignment guide and stiffer bristles.
Figure 8B:
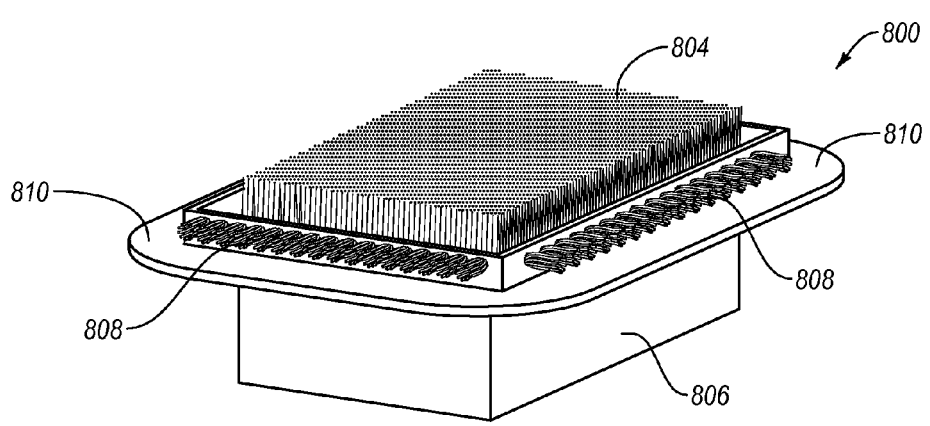

FIG. 8A illustrates two parts of a scrub brush 800 including a first part that includes a sponge 806 and softer bristles 804 (e.g., such as conventional surgical scrub-in brush 100 shown in FIG. 1) and a second part that includes finger alignment guide 810 and stiffer bristles 808. Providing a scrub brush in two parts as shown in FIG. 8A illustrates how different components of scrub brush 800 can be separately molded or manufactured and then joined together to form a single unit as shown in FIG. 8B. FIGS. 8A and 8B further show how scrub brush 800 can have an oval shape.

In any of the foregoing examples, the sponge or reservoir element may alternatively be impregnated with a degreasing or other appropriate cleaning composition to aid in removing foreign debris from a person's hands and fingers in a more industrialized setting. Thus, a scrub brush suitable for surgical scrub-in procedures can be used or modified for use in other settings where it is desirable to more reliably clean under a person's fingernails to provide enhanced sterility and/or cleaner looking hands and nails (e.g., mechanics, tire shop workers, industrial workers, gardeners, painters, food service professionals, lab technicians, and the like).

III. Examples

Example 1

A medical practitioner uses a state of the art surgical scrub-in device to clean and disinfect arms and hands but the fingernail pick is discarded. As a result, pathogens, dirt and debris remain in the gaps under fingernails with only superficial cleansing and disinfecting at the user's fingertips as a result of the gentle scrubbing action by the sponge and/or soft brush bristles used to clean arm and hands. This procedure is adequate for many situations so long as the gaps under the fingernails are not disrupted and/or the fingers are not submerged in bodily fluids or flushed with treatment solutions so as to dissolve or wash dirt, debris, bacteria and/or pathogens into the surgical site.

Even if the patient becomes infected, the manufacturer of the surgical scrub kit might avoid liability if the package containing the scrub-in brush and fingernail pick provides instructions to medical practitioners to first clean the gaps under the fingernails using the nail pick prior to using the scrub brush to wash and disinfect the arms and hands. One might postulate that including the nail pick and instructions is designed more to avoid liability than ensure sterile fingernails. Medical practitioners may also avoid liability unless it can be proven how a patient was infected (e.g., because the nail pick was not properly used or simply because causation may be impossible to prove).

There is no telling how many infections during or following surgery may have been caused by fingers that were not completely cleaned and sterilized prior to surgery. Because infection can occur at any stage during or following surgery, it may be impossible for anyone to know the impact of the failure of a medical practitioner to properly clean and sterilize the gaps under the fingernails prior to a surgical procedure. As a result, similar medical scrub-in devices and procedures have been followed for decades without change.

Example 2

The same surgical scrub-in device as in Example 1 is used but the fingernail pick is used as directed. All visible dirt is removed from the gaps underneath a medical practitioner's fingernails but microscopic pathogens remain lodged within the gap under one, some, or all the fingernails, even after washing the arms and hands using the supplied scrub brush and sponge. In some cases, the nail cleaning procedure is performed while the fingers are dry and without use of antiseptic or flowing water. Apart from removal of dirt, the existence of invisible pathogens may provide similar problems as if the fingernail pick were not used (e.g., as in Example 1). Worse, the lack of cleanliness and sterility may be exacerbated if the nail pick only dislodges and loosens dirt, pathogens, or debris but does not completely remove them prior to surgery. This may facilitate contamination of the surgical site, especially if the nail pick cross contaminates an initially clean nail bed of one finder with pathogens from a dirty or infected nail bed of another finger.

Example 3

An improved medical scrub device as described herein is used to more thoroughly clean, disinfect and sterilize the gaps under a medical practitioner's fingernails. As a result of a back and forth scrubbing action, coupled with the use of a disinfecting composition and/or running water, the fingernail cleaning bristles remove essentially all dirt or other debris and remove, or at least kill, all or substantially all pathogens that were or that remain underneath the person's fingernails. The fingernail cleaning procedure is greatly simplified compared to state of the art scrub-in devices and procedures that utilize a separate nail cleaning tool that must be used separately from the scrub-in brush.

The fingernail cleaning procedure using the disclosed devices can be performed using the same natural gripping action and back and forth motions as when scrubbing the user's arms and hands. This greatly speeds up and simplifies the nail cleaning and sterilization process, and uses antiseptic solution in same way, leading to greater compliance by medical practitioners and more completely sterilized fingernails, with the result being measurably cleaner and more sterile fingers, particularly the gaps under the fingernails. This, in turn, reduces the risk of patient contamination during surgical or other medical procedures as compared to procedures in which the gaps under a medical practitioner's fingernails are inadequately cleaned and sterilized, such as when a medical practitioner discards the fingernail pick packaged with a scrub-in brush or otherwise incompletely removes pathogens during the scrub-in process.

Comparative Examples

Scrub-in devices and procedures are performed according to Examples 1-3 and the hands are subsequently tested for sterility.

Comparative Example 4

After cleaning arms and hands according to Example 1, the gaps under all fingernails are tested for existence of pathogens. Detection tests and/or cultures known in the art determine that sufficient quantities of pathogens remain which are capable of causing or spreading disease during a subsequent medical procedure.

Comparative Example 5

After cleaning arms and hands according to Example 2, the gaps under all fingernails are tested for existence of pathogens. Detection tests and/or cultures known in the art determine that sufficient quantities of pathogens remain at least some of the time, which are capable of causing or spreading disease during a subsequent medical procedure. The tendency of pathogens to migrate from the gaps under a medical practitioner's fingernails to the patient may be increased if the nail pick is inadequately used and pathogens are only loosened but not removed and/or killed.

Comparative Example 6

After cleaning arms and hands according to Example 3, the gaps under all fingernails are tested for existence of pathogens. Detection tests and/or cultures known in the art determine that all or substantially all pathogens are removed and/or killed as a result of more complete cleaning and/or sterilization resulting from the combined effects of the scrubbing action by the fingernail cleaning bristles and the pathogen cleaning action by the antiseptic composition. The result is reduced cause or spread of disease during a subsequent medical procedure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A scrub brush for cleaning arms, hands, and fingernails, comprising:

a reservoir body comprising an absorbent material capable of absorbing and holding therein a cleaning composition;

a plurality of arm and hand scrubbing bristles extending laterally relative to a surface of the reservoir body, wherein the arm and hand scrubbing bristles have a first stiffness that promotes gentle cleansing of skin surfaces of a person's arms and hands during a cleansing procedure without scratching, gouging, scraping or otherwise damaging the skin;

a plurality of fingernail cleaning bristles having a second stiffness greater than the first stiffness of the arm and hand scrubbing bristles in order to more aggressively scrub dirt, pathogens, or other foreign debris from gaps underneath a person's fingernails when the person's fingers are moved back and forth relative to the fingernail cleaning bristles;

a two-part structural body interconnecting the arm and hand scrubbing bristles with the reservoir body wherein the arm and hand scrubbing bristles are formed on a first part of the two-part structural body, wherein the fingernail cleaning bristles are formed separately on a second part of the two-part structural body, and wherein the second part is and thereafter attached to the first part of the two-part structural body; and at least one finger guide surface adjacent to the fingernail cleaning bristles and positioned so as to maintain alignment between a person's fingernails and the fingernail cleaning bristles so that tips of the fingernail cleaning bristles enter gaps underneath the person's fingernails when the person's fingers are moved back and forth relative to the fingernail cleaning bristles during use.

2. A scrub brush as in claim 1, wherein the reservoir body comprises a flexible open cell foam and include an anti-infective composition impregnated therein.

3. A scrub brush as in claim 2, wherein the anti-infective composition comprises at least one antiseptic selected from the group consisting of betaine, chlorhexidine glutamate, iodine, povidone iodine, parachlorometaxylenol, chloroxylenol, triclosan, alcohols, quaternary ammonium compounds, cationic surfactants, anionic surfactants, phenol, polyhexanide, sodium chloride, boric acid, hydrogen peroxide, sodium hypochlorite, and terpenes.

4. A scrub brush as in claim 1, wherein the structural body first part and the arm and hand scrubbing bristles are co-molded as a single continuous polymer body.

5. A scrub brush as in claim 1, wherein the arm and hand scrubbing bristles comprise uniform rows and columns of individual bristles extending laterally from a surface of the structural body first part.

6. A scrub brush as in claim 1, wherein the fingernail cleaning bristles extend laterally from a surface of the structural body second part.

7. A scrub brush as in claim 1, wherein the fingernail cleaning bristles are co-molded with the structural body second part.

8. A scrub brush as in claim 1, wherein the fingernail cleaning bristles are molded from the same polymer as the arm and hand scrubbing bristles and are more stiff and rigid than the arm and hand scrubbing bristles as a result of at least one of having shorter length, thicker diameter, closer spacing, or different surface treatment compared to the arm and hand scrubbing bristles.

9. A scrub brush as in claim 1, wherein the at least one finger guide surface comprises a substantially smooth and rigid surface having minimal friction so as to facilitate slippage of fingers across the finger guide surface in a back and forth motion during a fingernail cleaning process.

10. A scrub brush as in claim 1, wherein the at least one finger guide surface comprises a single guide surface.

11. A scrub brush for cleaning arms, hands, and fingernails, comprising:
a structural body having a main wall and an outer sidewall attached to and extending laterally from the main wall;
a reservoir body adjacent to the structural body comprising an absorbent material, wherein the main wall of the structural body is positioned alongside a first side of reservoir body and the outer sidewall of the structural body is positioned alongside at least a portion of a second side of the reservoir body approximately perpendicular to the first side of the reservoir body;
a plurality of arm and hand scrubbing bristles extending laterally from the main wall of the structural body and away from the first side of the reservoir body, wherein the arm and hand scrubbing bristles have a first stiffness that promotes gentle cleansing of skin surfaces of a person's arms and hands during a cleansing procedure without scratching, gouging, scraping or otherwise damaging the skin;
a plurality of fingernail cleaning bristles attached to and extending laterally from a surface of the outer sidewall of the structural body and positioned outwardly relative to the second side of the reservoir body, the fingernail cleaning bristles having a second stiffness greater than the first stiffness of the arm and hand scrubbing bristles in order to more aggressively scrub dirt, pathogens, or other foreign debris from gaps underneath a person's fingernails when the person's fingers are moved back and forth relative to the fingernail cleaning bristles; and
at least one finger guide surface provided by or extending from a surface of the outer sidewall of the structural body and positioned so as to provide separation between a person's fingers and the second side of the reservoir body while maintaining alignment between a person's fingernails and the fingernail cleaning bristles so that tips of the fingernail cleaning bristles enter gaps underneath the person's fingernails when the person's fingers are moved back and forth relative to the fingernail cleaning bristles during use.

12. A scrub brush as in claim 11, wherein the at least one finger guide surface comprises a pair of guide surfaces spaced apart and positioned so as to form a finger guide channel within which the fingernail cleaning bristles are positioned.

13. A scrub brush as in claim 11, further comprising a cleaning composition absorbed within the absorbent material of the reservoir body.

14. A scrub brush for cleaning arms, hands, and fingernails, comprising:
a structural body having a main wall and at least one sidewall attached to and extending laterally from the main wall so as to form an outer perimeter of the structural body;
a reservoir body adjacent to the structural body comprising an absorbent material;
a plurality of arm and hand scrubbing bristles extending from the main wall of the structural body, wherein the arm and hand scrubbing bristles have a first stiffness that promotes gentle cleansing of skin surfaces of a person's arms and hands during a cleansing procedure without scratching, gouging, scraping or otherwise damaging the skin;
a plurality of fingernail cleaning bristles extending outwardly from the at least one sidewall and positioned around the outer perimeter of the structural body, the fingernail cleaning bristles having a second stiffness greater than the first stiffness of the arm and hand scrubbing bristles in order to more aggressively scrub dirt, pathogens, or other foreign debris from gaps underneath a person's fingernails when the person's fingers are moved back and forth relative to the fingernail cleaning bristles; and
at least one finger guide surface provided by or extending from the at least one sidewall of the structural body and positioned so as to maintain alignment between a person's fingernails and the fingernail cleaning bristles so that tips of the fingernail cleaning bristles enter gaps underneath the person's fingernails when the person's fingers are moved back and forth relative to the fingernail cleaning bristles during use.

15. A scrub brush as in claim 14, wherein the scrub brush is oval and/or the reservoir body has a convex or concave surface.

16. A scrub brush for cleaning arms, hands, and fingernails, comprising:
a reservoir body comprising an absorbent material capable of absorbing and holding therein a cleaning composition;
a plurality of arm and hand scrubbing bristles extending laterally relative to a surface of the reservoir body, wherein the arm and hand scrubbing bristles have a first stiffness that promotes gentle cleansing of skin surfaces of a person's arms and hands during a cleansing procedure without scratching, gouging, scraping or otherwise damaging the skin;
a plurality of fingernail cleaning bristles having a second stiffness greater than the first stiffness of the arm and hand scrubbing bristles in order to more aggressively scrub dirt, pathogens, or other foreign debris from gaps underneath a person's fingernails when the person's fingers are moved back and forth relative to the fingernail cleaning bristles; and
a pair of spaced apart finger guide surfaces adjacent to the fingernail cleaning bristles and forming a finger guide channel within which the fingernail cleaning bristles are positioned so as to maintain alignment between a person's fingernails and the fingernail cleaning bristles so that tips of the fingernail cleaning bristles enter gaps underneath the person's fingernails when the person's fingers are moved back and forth relative to the fingernail cleaning bristles during use.

17. A scrub brush as in claim 16, further comprising a structural body interconnecting the arm and hand scrubbing bristles and the reservoir body and wherein the fingernail cleaning bristles and the arm and hand scrubbing bristles are co-molded with the structural body but formed from different polymers, wherein the arm and hand scrubbing bristles are formed from a first polymer and the fingernail cleaning bristles are formed from a second polymer having greater stiffness and/or rigidity than the first polymer.

18. A scrub brush as in claim 16, wherein the fingernail cleaning bristles are oriented at a first average angle between about 0-45° relative to a second average angle of the arm and hand scrubbing bristles.

19. A scrub brush as in claim 16, wherein the fingernail cleaning bristles are oriented at a first average angle between about 45-135° relative to a second average angle of the arm and hand scrubbing bristles.

20. A scrub brush as in claim 16, wherein the fingernail cleaning bristles are oriented at a first average angle between about 45-225° relative to a second average angle of the arm and hand scrubbing bristles.

* * * * *

UNITED STATES PATENT AND TRADEMARK OFFICE
CERTIFICATE OF CORRECTION

PATENT NO. : 9,095,373 B2  
APPLICATION NO. : 13/855393  
DATED : August 4, 2015  
INVENTOR(S) : Guynn et al.

Page 1 of 1

It is certified that error appears in the above-identified patent and that said Letters Patent is hereby corrected as shown below:

IN THE SPECIFICATION

Column 1  
Line 53, change "resulting on" to --resulting in--

Column 3  
Line 51, change "FIG. 1A" to --FIG. 2A--

Column 5  
Line 24, change "piassaya" to --piassava--

Column 7  
Line 54, change "structural body can" to --structural body 202 can--

Column 9  
Line 5, change "bottom surface 222 of" to --bottom surface of--

Column 12  
Line 57, change "platform 644" to --platform 642--

Signed and Sealed this  
First Day of March, 2016

Michelle K. Lee  
*Director of the United States Patent and Trademark Office*